United States Patent [19]
Razdan et al.

[11] 3,987,190
[45] Oct. 19, 1976

[54] METHOD OF TREATING HYPERTENSION WITH, AND COMPOSITIONS USEFUL THEREIN CONTAINING, A 4H-THIENO[2,3-C][1]BENZOPYRAN OR A 3H,5H-THIOPYRANO[2,3-C][1]BENZOPYRAN

[75] Inventors: Raj Kumar Razdan, Belmont; Harry George Pars, Lexington, both of Mass.

[73] Assignee: Sharps Associates, Cambridge, Mass.

[22] Filed: Feb. 18, 1975

[21] Appl. No.: 550,292

Related U.S. Application Data

[63] Continuation-in-part of Ser. No. 210,170, Dec. 20, 1971, Pat. No. 3,883,551, which is a continuation-in-part of Ser. No. 852,928, Aug. 25, 1969, abandoned.

[52] U.S. Cl. .............................................. 424/275
[51] Int. Cl.² ......................................... A61K 31/38
[58] Field of Search ................................... 424/275

[56] References Cited
UNITED STATES PATENTS

| | | | |
|---|---|---|---|
| 3,462,458 | 8/1969 | McIntyre | 260/343.2 |
| 3,467,675 | 9/1969 | Petersen et al. | 260/346.2 |

*Primary Examiner*—James O. Thomas, Jr.
*Assistant Examiner*—Daren M. Stephens
*Attorney, Agent, or Firm*—Merriam, Marshall, Shapiro & Klose

[57] ABSTRACT

A method of reducing blood pressure in a hypertensive mammalian patient by administering 1,2-dihydro-4,4-dimethyl-9-hydroxy-7-(3-methyl-2-octyl)-4H-thieno[2,3-c][1]benzopyran or 1,2-dihydro-5,5-dimethyl-10-hydroxy-8-(3-methyl-2-octyl)-3H,5H-thiopyrano-8 2,3-c][1]benzopyran. Pharmaceutical compositions containing 1,2-dihydro-4,4-dimethyl-9-hydroxy-7-(3-methyl-2-octyl)-4H-thieno[2,3-c][1]benzopyran or 1,2-dihydro-5,5-dimethyl-10-hydroxy-8-(3-methyl-2-octyl)-3H,5H-thiopyrano[2,3-c][1]benzopyran dispersed in a pharmaceutical carrier.

6 Claims, No Drawings

METHOD OF TREATING HYPERTENSION WITH, AND COMPOSITIONS USEFUL THEREIN CONTAINING, A 4H-THIENO2,3-c1BENZOYRAN OR A 3H,5H-THIOPYRANO2,3-c1BENZOPYRAN

This application is a continuation-in-part of our co-pending application Ser. No. 210,170 filed Dec. 20, 1971, now U.S. Pat. No. 3,883,551 issued May 13, 1975, which in turn is a continuation-in-part of our application Ser. No. 852,928 filed Aug. 25, 1969, now abandoned.

This invention relates to a method of treating hypertension using 1,2-dihydro-4,4-dimethyl-9-hydroxy-7-(3-methyl-2-octyl)-4H-thieno[2,3-c] [1]benzopyran or 1,2-dihydro-5,5-dimethyl-10-hydroxy-8-(3-methyl-2-octyl)-3H,5H-thiopyrano[2,3-c] [1]benzopyran as an anti-hypertensive agent, and to pharmaceutical compositions containing the compounds.

According to the present invention it has been discovered that 1,2-dihydro-4,4-dimethyl-9-hydroxy-7-(3-methyl-2-octyl)-4H-thieno[2,3-c] [1]benzopyran (compound I) and 1,2-dihydro-5,5-dimethyl-10-hydroxy-8-(3-methyl-2-octyl)-3H, 5H-thiopyrano[2,3-c] [1]benzopyran (compound II) each have anti-hypertensive activity when administered to a patient. Each compound substantially reduces the blood pressure when administered to a mammalian patient suffering from hypertension.

Compound I has the formula

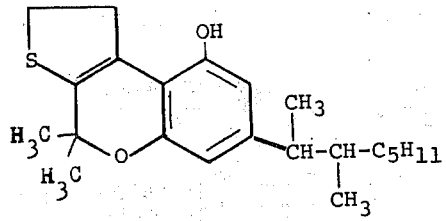

I and compound II has the formula

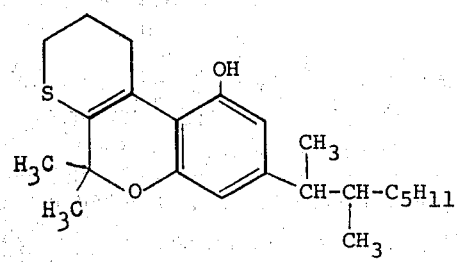

II

The anti-hypertensive activity of each of the compounds useful in the practice of this invention has been demonstrated in genetically hypertensive rats. However, the compounds have minimal direct cardiovascular effects in normotensive animals at therapeutic dosages.

The anti-hypertensive activity of the compounds was demonstrated in genetically hypertensive (spontaneously hypertensive) rats of the Okamoto strain trained to be restrained in a wire mesh cylinder for measurement of blood pressure by an indirect procedure. Half an hour prior to blood pressure measurement, the rats were placed in a warm chamber maintained at a constant temperature of 36° C. An occluding cuff, attached to a programmed sphygmomanometer, was placed near the base of the tail of each rat and the pressure in the cuff was increased automatically from 0 to 250 mm Hg at a rate of 10 mm Hg per second. The cuff was then deflated at the same rate. The total time required for each cycle of inflation and deflation of the cuff was 50 seconds, and the interval between successive cycles was 1 minute. A photocell was placed distal to the cuff to sense the arterial pulse wave. As pressure in the cuff increased, the pulse wave completely disappeared when the cuff pressure just exceeded the systolic arterial blood pressure. During deflation, the pulse wave reappeared at approximately the same pressure. Five interference-free signals obtained during deflation were recorded for each rat. Only those rats with a systolic blood pressure of 180 mm Hg or more during the control period were used in the study. A model 7 Grass polygraph was used to record the blood pressure of the rats.

Compound I was tested in two rats, using the above procedure, at an oral dosage of 10 mg/kg and recordings were made at 4 hour and 24 hour intervals. The following results were obtained:

| Rat No. | Per Cent Change In Blood Pressure | |
|---|---|---|
| | 4 Hours | 24 Hours |
| 1 | −31 | −18 |
| 2 | −17 | −02 |

Compound II was tested, in four rats, using the above procedure, at an oral dosage of 3 mg/kg and control, 3 hour and twenty-four hour interval blood pressure readings were recorded. The following results were obtained:

| Rat No. | Control Blood Pressure (mm Hg) | Per Cent Change In Blood Pressure | |
|---|---|---|---|
| | | 3 Hours | 24 Hours |
| 1 | 179 | −21 | − 9 |
| 2 | 189 | −27 | −16 |
| 3 | 192 | −24 | −11 |
| 4 | 176 | −14 | − 9 |

Compound II was also tested orally at 10 mg/kg in two rats with the following results:

| Rat No. | Per Cent Change In Blood Pressure | | |
|---|---|---|---|
| | 4 Hours | 24 Hours | 48 Hours |
| 1 | −15 | −30 | −19 |
| 2 | −21 | −28 | −23 |

In the practice of this invention compound I or compound II can be administered to hypertensive mammalian patients in dosages of 0.01 to 40 mg./kg. of body weight daily, preferably in divided dosages, i.e., three to four times daily. Each compound exhibits anti-hypertensive activity when administered by the oral route and the parenteral, i.e., intravenous, intramuscular or intraperitoneal, route. The oral route is the preferred route of administration.

Although either compound I or II can be administered in pure undiluted form, it is advisable to first combine it with a suitable pharmaceutical carrier or adjuvant to attain a more satisfactory size to dosage relationship.

Solid pharmaceutical carriers such as calcium carbonate, starch, sugar, talc and the like may be used to form powders. The powders may be used as such or be tableted or be used to fill capsules. Suitable lubricants like magnesium stearate, binders such as gelatin and disintegrating agents like sodium carbonate in combination with citric acid may be used to form the tablets. Care in the choice of solid carriers and other ingredients should be exercised to avoid reaction of the active agent with the excipients.

Unit-dosage forms such as tablets and capsules may contain any suitable predetermined amount of compound I or II and can be administered one or more at a time at regular intervals. Such forms should generally contain a minimum concentration of 0.1% by weight of active agent, and particularly 1 to 75 mg., and desirably 1 to 20 mg., of active agent.

A typical tablet can be prepared from a mixture of 89.0 g. of mannitol, 4.0 g. of Carbopol-934 (a binder disclosed in U.S. Pat. No. 2,909,462), 16.5 g. of compound I or II, and 2.5 g. of stearic acid. The mixture is blended by passage through a No. 20 screen and slugged in the usual way on a tablet slugging machine. The slugs are ground through a No. 20 screen and compressed into tablets using a ¼ inch punch and die. This formulation is for 1000 tablets. Each tablet is to contain 16.5 mg. of compound I or II.

The compounds can also be formulated for administration in liquid form and used for intramuscular injection. Still further, the compounds can be formulated for oral administration in aqueous alcohol, glycol or oil solutions or oil-water emulsions in the same manner as conventional medicinal substances are prepared.

The following examples are presented to illustrate chemical methods of making compounds I and II.

EXAMPLE 1

1,2-Dihydro-4,4-dimethyl-9-hydroxy-7-(3-methyl-2-octyl)-4H-thieno[2,3-c][1]benzopyran

A. Methyl 3-oxo-2,3,4,5-tetrahydrothiophene-2-carboxylate

The procedure of Woodward and Eastman (J. Amer. Chem. Soc. 68, 2229 (1946) was followed for the cyclization of 100 g. (0.55 mole) of methyl 3-(methoxycarbonylmethylthio) propionate to give 56 g. (65%) of methyl 3-oxo-2,3,4,5-tetrahydrothiophen-2-carboxylate. NMR spectral analysis showed the product to be a mixture of isomers having the composition of 80% of the desired product

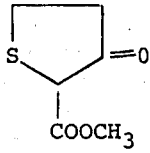

and 20% of methyl 4-oxo-2,3,4,5-tetrahydrothiophen-3-carboxylate

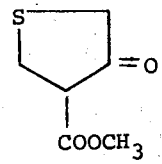

which could be isolated by fractional distillation.

B. 1,2-Dihydro-9-hydroxy-7-(3-methyl-2-octyl)-4-oxo-4H-thieno-[2,3-c][1]benzopyran A solution of 2.5 g. (0.011 mole) of 5-(3-methyl-2-octyl)resorcinol and 2.0 g. (0.013 mole) of methyl 3-oxo-2,3,4,5-tetrahydrothiophene-2-carboxylate in 50 ml. of absolute ethanol in a three-necked flask equipped with drying tube was cooled in an ice-water bath and saturated with dry hydrogen chloride. The 5-(3-methyl-2-octyl) resorcinol was prepared according to the method of Adams, MacKenzie and Loewe (J. Amer. Chem. Soc. 70, 664-8 (1948)). The reaction mixture was allowed to stand for three days at room temperature, during which time a heavy yellow solid formed. The hydrogen chloride was evaporated, the mixture was concentrated and the solid was filtered and washed with ethanol. The yield of the crude benzopyrone thus obtained was 2.6 g. (59%), m.p. 190°–205° C.

Repeated crystallization from absolute ethanol gave an analytical sample, m.p. 209°–212° C, of the compound

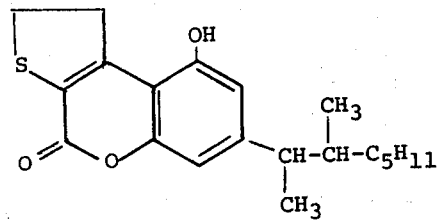

Anal. Calcd. for $C_{20}H_{26}O_3S$: C, 69.36; H, 7.51; S, 9.25. Found: C, 69.15; H, 7.41; S, 9.30.

C. 1,2-Dihydro-4,4-dimethyl-9-hydroxy-7-(3-methyl-2-octyl)-4H-thieno[2,3-c][1]benzopyran The Grignard reagent was prepared by bubbling bromomethane into a mixture of 7.2 g. (0.3 mole) of magnesium turnings in ether. When all the magnesium had reacted, the solution was refluxed for a short time to remove the excess bromomethane. A solution of 9.0 g. (0.026 mole) of 1,2-dihydro-9-hydroxy-7-(3-methyl-2-octyl)-4-oxo-4H-thieno[2,3-c][1]benzopyran in 250 ml. of benzene was added to the methylmagnesium bromide and the reaction mixture was kept at 45° C for 24 hours. After the addition of saturated ammonium chloride, the benzene/ether layer was separated, and the aqueous layer was extracted with ether. The combined organic layers were washed with water, dried over sodium sulfate and evaporated to give a greenish, gummy residue. The material was shown to be pure by thin-layer chromatography (TLC) (10% MeOH/CHCl₃); and the IR and NMR spectra indicated the compound to be 5-(3-methyl-2-octyl)-2-[4,5-dihydro-2-(2-hydroxy-2-propyl)-thien-3-yl]resorcinol (triol).

2.0 g. of the triol was dissolved in benzene and refluxed for 3 hours in the presence of a small amount of p-toluenesulfonic acid. The benzene solution was concentrated and the residue was chromatographed using activated magnesium silicate column support, 60–100 mesh, and graded ether/petroleum ether solvent mixtures. The IR, UV and NMR spectra confirmed the desired structure.

Anal. Calcd. for $C_{22}H_{32}O_2S$: C, 73.33; H, 8.91; S, 8.91. Found: C, 73.10; H, 9.16, S, 8.75.

The gum exhibited $\lambda_{max}^{EtOH}$ 320 m$\mu$ (log$\epsilon$ 3.951). IR, UV and NMR spectra confirmed the pyran structure.

EXAMPLE 2

1,2-Dihydro-5,5-dimethyl-10-hydroxy-8-(3-methyl-2-octyl)-3H,5H-thiopyrano[2,3-c] [1]benzopyran

A. Methyl 3-oxo-2,3,4,5-tetrahydro-6H-thiopyran-2-carboxylate

The procedure of Leonard and Figueras (J. Amer. Chem. Soc. 74, 917 (1952)) was followed for the cyclization of 20 g. of carbomethoxymethyl γ-carbomethoxypropyl sulfide to give 11.1 g. (70%) of methyl 3-oxo-2,3,4,5-tetrahydro-6H-thiopyran-2-carboxylate. The structure was confirmed by IR and NMR spectra.

B. 1,2-Dihydro-10-hydroxy-8-(3-methyl-2-octyl)-5-oxo-3H,5H-thiopyrano[2,3-c] [1]benzopyran A solution of 14.2 g. (0.06 mole) of 5-(3-methyl-2-octyl)resorcinol and 11.1 g. (0.063 mole) of methyl 3-oxo-2,3,4,5-tetrahydro-6H-thiopyran-2-carboxylate in 90 ml. of absolute ethanol was cooled in an ice-salt bath and saturated with anhydrous hydrogen chloride. After standing for 2 days at room temperature, the ethanol was removed on a rotary evaporator. The residue was dissolved in ether, washed with sodium bicarbonate solution and dried over sodium sulfate. Evaporation of the solvent gave 28.0 g. of residue which was chromatographed using activated magnesium silicate (60–100 mesh) and graded methanol/chloroform solvent mixtures. A total of 10 g. of crude solid was obtained from the 1% methanol/chloroform fractions. The material was recrystallized twice from ethyl acetate/hexane to give 8.5 g. (40%) colorless crystals, m.p. 131°–133° C. The proposed structure was confirmed by IR and NMR spectra.

C. 1,2-Dihydro-5,5-dimethyl-10-hydroxy-8-(3-methyl-2-octyl)-3H,5H-thiopyrano[2,3-c] [1]benzopyran Methylmagnesium bromide was prepared by bubbling bromomethane into a mixture of 7.68 g. (0.32 mole) of magnesium turnings in ether. When all the magnesium had reacted, the solution was refluxed for a short time to remove the excess bromomethane. A solution of 6.96 g. (0.02 mole) of the pyrone (prepared as above) in benzene was added and the reaction mixture was kept at 45° C for 24 hours. The reaction mixture was decomposed with saturated ammonium chloride; the organic layer was separated and the aqueous layer was extracted twice with ether. The organic layers were combined, washed with water, dried and evaporated to give a gummy residue. The IR and NMR spectra indicated the compound to be 5-(3-methyl-2-octyl)-2-[4,5-dihydro-2-(2-hydroxy-2-propyl)-6H-thiopyran-3-yl]resorcinol.

A small quantity of p-toluenesulfonic acid was added to a benzene solution of the above triol and the mixture was heated at reflux for 1-½ hours in the presence of nitrogen. The benzene solution was washed with sodium bicarbonate solution, dried over sodium sulfate and evaporated to give a greenish-brown residue. Chromatography using activated magnesium silicate (60–100 mesh) and graded ether/petroleum ether solvent mixtures gave 5.2 g. (60%) of a nearly colorless gum. The gum exhibited $\lambda_{max}^{EtOH}$ 305 m$\mu$ (log$\epsilon$ 4.262) and the IR, NMR and UV spectra confirmed the structure as 1,2-dihydro-5,5-dimethyl-10-hydroxy-8-(3-methyl-2-octyl)-3H,5H-thiopyrano[2,3-c] [1]benzopyran.

Anal. Calcd. for $C_{23}H_{34}O_2S$: C, 73.73; H, 9.15; S, 8.54. Found: C, 73.55; H, 9.12; S, 8.45.

The foregoing detailed description has been given for clearness of understanding only, and no unnecessary limitations should be understood therefrom, as modifications will be obvious to those skilled in the art.

What is claimed is:

1. A pharmaceutical composition containing 1 to 75 mg. of 1,2-dihydro-4,4-dimethyl-9-hydroxy-7-(3-methyl-2-octyl)-4H-thieno[2,3-c] [1]benzopyran or 1,2-dihydro-5,5-dimethyl-10-hydroxy-8-(3-methyl-2-octyl)-3H,5H-thiopyrano[2,3-c] [1]benzopyran dispersed in a pharmaceutical carrier.

2. A pharmaceutical composition according to claim 1 in the form of a unit dosage tablet.

3. A pharmaceutical composition according to claim 1 in the form of a unit dosage capsule.

4. A pharmaceutical composition according to claim 1 in unit dosage form containing 1 to 20 mg. of either of the named compounds.

5. A method of reducing blood pressure in a hypertensive mammalian patient, in need of blood pressure reduction, comprising administering to said patient a therapeutically effective amount of 1,2-dihydro-4,4-dimethyl-9-hydroxy-7-(3-methyl-2-octyl)-4H-thieno[2,3-c] [1]benzopyran or 1,2-dihydro-5,5-dimethyl-10-hydroxy-8-(3-methyl-2-octyl)-3H,5H-thiopyrano[2,3-c] [1]benzopyran to reduce the blood pressure of the patient.

6. The method of claim 5 in which 0.01 to 40 mg./kg. of body weight of one of the named compounds is administered daily.

* * * * *

UNITED STATES PATENT AND TRADEMARK OFFICE
CERTIFICATE OF CORRECTION

PATENT NO. : 3,987,190
DATED : October 19, 1976
INVENTOR(S) : Raj Kumar Razdan et al.

It is certified that error appears in the above-identified patent and that said Letters Patent are hereby corrected as shown below:

Abstract, <u>line 6</u>, change "-8 2,3-c]" to -- [2,3-c] --; column 1, <u>line 4 of the title</u>, change "2,3-cl" to -- [2,3-C][1] --; <u>line 5 of the title</u>, change "2,3-cl" to -- [2,3-C][1] --.

Signed and Sealed this

Fourteenth Day of December 1976

[SEAL]

Attest:

RUTH C. MASON
*Attesting Officer*

C. MARSHALL DANN
*Commissioner of Patents and Trademarks*